US006790434B2

(12) United States Patent
Borchert et al.

(10) Patent No.: US 6,790,434 B2
(45) Date of Patent: *Sep. 14, 2004

(54) TOPICAL COSMETIC COMPOSITION

(75) Inventors: Stefan Borchert, Berlin (DE);
Rolf-Dieter Petersen, Berlin (DE)

(73) Assignee: Chemisches Laboratorium Dr. Kurt Richter GmbH, Berlin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 10/013,003

(22) Filed: Nov. 5, 2001

(65) Prior Publication Data

US 2002/0168388 A1 Nov. 14, 2002

(30) Foreign Application Priority Data

Feb. 23, 2001 (EP) .............................. 01104601

(51) Int. Cl.$^7$ ............................ A61K 7/42; A61K 7/44; A61K 7/00; A61K 35/78
(52) U.S. Cl. .......................... 424/59; 424/60; 424/400; 424/401; 424/725
(58) Field of Search ............................ 424/59, 60, 400, 424/401, 196.1, 725

(56) References Cited

U.S. PATENT DOCUMENTS

| 4,464,362 A | * | 8/1984 | Kludas et al. ............... 424/195 |
| 5,114,848 A | | 5/1992 | Pares Farras et al. ....... 435/101 |
| 5,547,997 A | * | 8/1996 | Kludas ........................ 514/773 |
| 6,270,811 B1 | | 8/2001 | Fregonese .................... 424/780 |

FOREIGN PATENT DOCUMENTS

| EP | 0043128 A1 | 1/1982 | ............ A61K/7/48 |
| EP | 0668072 A1 | 8/1995 | ............ A61K/7/48 |
| EP | 1120108 A1 | 8/2001 | ............ A61K/7/48 |
| FR | 2696932 A1 | 4/1994 | ............ A61K/7/48 |
| JP | 1242532 | 9/1989 | ........... A61K/35/74 |
| WO | WO 9823243 | 6/1998 | |

OTHER PUBLICATIONS

Baadsgaard, O., "In vivo Ultraviolet Irradiation Of Human Skin Results In Profound Perturbation Of The Immune System", *Arch. Dermatol.* 127:99–109, 1991.

Daniels, F., Jr. et al., "Histochemical Responses Of Human Skin Following Ultraviolet Irradiation", *J. Invest. Dermatol.* 37:351–356, 1961.

Denkins, Y.D. et al., "Exposure Of Mice To UV–B Radiation Suppresses Delayed Hypersensitivity To *Candida albicans*", *Photochem. Photobiol.* 49:615–619, 1989.

Fisher, G.J. and J.J. Voorhees, "Molecular Mechanisms Of Photoaging And Its Prevention By Retinoic Acid: UVR Induces MAP Kinase Signal Transduction Cascades That Induce AP–1–Regulated Matrix Metalloproteinases That Degrade Human Skin In Vivo", *J. Invest. Dermatol. Symp. Proc.* 3: 61–68, 1998.

Giannini, "Suppression Of Pathogenesis In Cutaneous Leishmaniasis By UV Irradiation", *Infection And Immunity*, 838–843, 1986.

Iwai, I et al.,. "UVA–Induced Immune Suppression Through An Oxidation Pathway",*J. Invest. Dermatol.* 112 (1):19–24, 1999.

Jeevan, A. and M.L. Kripke, "Effect Of A Single Exposure To Ultraviolet Radiation On Mycobacterium Bovis Bacillus Calmette–Guerin Infection In Mice", *J. Immunol.* 143:2837–2843, 1989.

Kane, D.J. et al., "Bcl–2 Inhibition Of Neural Cell Death: Decreased Generation Of Reactive Oxygen Species", *Science* 262:1274–1276, 1993.

Kripke, M.L, "Immunological Unresponsiveness Induced By UV Radiation", *Immunol. Rev.* 80:87–102, 1984.

Kvam, E. and R.M. Tyrrell, "Induction Of Oxidative DNA Base Damage In Human Skin Cells By UV And Near Visible Radiation", *Carcinogenesis* 18:2379–2384, 1997.

Levy, S. and L.A. Staehelin, "Synthesis, Assembly And Function Of Plant Cell Wall Macromolecules", *Current Opinion in Cell Biology* 4:856–862, 1992.

Lynch, D.H. et al., "Fas And FasL In The Homeostatic Regulation Of Immune Responses", *Immunol. Today* 16:569–574, 1995.

Miller, E. J., "Structural Studies On Cartilage Collagen Employing Limited Cleavage And Solubilization With Pepsin", *Biochem.* 11:4903–4909, 1972.

Nishigori et al., "Evidence That DNA Damage Triggers Interleukin 10 Cytokine Production In UV–irradiated Murine Keratinocytes", *Proc. Natl. Acad. Sci. USA* 93:10354–59, 1996.

(List continued on next page.)

Primary Examiner—Shelley A. Dodson
(74) Attorney, Agent, or Firm—Fish & Neave; James F. Haley, Jr.; Li Su

(57) ABSTRACT

The invention relates to cosmetic compositions for topical application for counteracting UV radiation induced skin damage comprising as active substances a first component which comprises inactivated bacteria selected from the group consisting of the genus Bifidobacterium, Actinomycetaceae, Propionimycetaceae, Lactobacillaceae and Coryneform bacteria and a second component which comprises an extract of plant extracellular matrix. Preferably, the plant extracellular matrix is selected from the group consisting of glycoproteins, carbohydrate polymers and arabinogalactan proteins. Processes for using the cosmetic compositions are also described.

20 Claims, 6 Drawing Sheets

OTHER PUBLICATIONS

Otani, T. and R. Mori, "The Effects Of Ultraviolet Irradiation Of The Skin On Herpes Simplex Virus Infection: Alteration In Immune Function Mediated By Epidermal Cells And In The Course Of Infection", *Arch. Virol.* 96:1–15, 1987.

Rattis et al., "Effects Of UVB Radiation On Human Langerhans Cells: Functional Alteration Of CD 86 Upregulation And Induction Of Apoptotic Cell Death", *J. Invest. Dermatol.* 111:373–379, 1998.

Roberts, K., "The Plant Extracellular Matrix", *Current Opinion In Cell Biology* 1:1020–1027, 1989.

Roberts, K., "Structures At The Plant Cell Surface" *Current Opinion In Cell Biology* 2:920–928, 1990.

Sanders, L.C. et al., "A Homolog Of The Substrate Adhesion Molecule Vitronectin Occurs In Four Species Of Flowering Plants", *Plant Cell* 3:629–635, 1991.

Shreedhar, V. et al., "A Cytokine Cascade Including Prostaglandin E2, IL–4, And IL–10 Is Responsible For UV–Induced Systemic Immunce Suppression", *J. Immunol.* 160 (8):3783–3789, 1998.

Teunissen, M.B.M., "Dynamic Nature And Function Of Epidermal Langerhans Cells In Vivo And In Vitro: A Review, With Emphasis On Human Langerhans Cells", *Histochem. J* 24:697–716, 1992.

Wang, Y. et al., "Differential Regulation Of P53 And Bcl–2 Expression By UV A And B", *J. Invest. Dermatol.* 111:380–384, 1998.

Young, A.R., "The Sunburn Cell", *Photodermatol.* 4:127–134, 1987.

Zhang, R. et al., "Enhancement Of Immune Function In Mice Fed High Doses Of Soy Daidzein", *Nutrition and Cancer* 29 (1):24–28, 1997.

* cited by examiner

TOPICAL COSMETIC COMPOSITION

TECHNICAL FIELD OF THE INVENTION

The invention relates to cosmetic compositions for topical application for counteracting UV radiation induced skin damage comprising as active substances a first component obtained from inactivated cultures of a bacteria selected from the genus Bifidobacterium, Actinomycetaceae, Propionimycetaceae, Lactobacillaceae and Coryneform bacteria and a second component which is an extract of plant extracellular matrix. Preferably, the plant extracellular matrix is selected from the group consisting of glycoproteins, carbohydrate polymers and arabinogalactan proteins. Processes for using the cosmetic compositions are also described.

BACKGROUND OF THE INVENTION

Exposure of skin to UV radiation can cause diverse biological effects, including sunburn (inflammation), induction of skin cancer (melanoma), premature skin aging and alteration in cutaneous immune cells (immunosuppression) all leading to (permanent) damage of the skin cells. Skin cell damage due to UV is induced by several mechanisms, such as UV-induced immunosuppression, UV-induced DNA-damage and accumulation of DNA-damage.

Immunosuppression is a status of immunological imbalance of the skin (Kripke, 1984; Baadsgard, 1991). It is known that cutaneous exposure to UVB (280–320 nm) radiation induces systemic suppression of T-cell mediated contact hypersensitivity (CHS) to haptens and delayed type hypersensitivity (DTH) responses to protein antigens such as *Herpes simplex* virus, *Candida albicans* or mycobacteria (Otani et al., 1987; Giannini, 1986; Denkins et al., 1989; Jeevan et al., 1989). Especially Langerhans cells (LC) which are highly specialized antigen-presenting cells (APC) play an essential role in the induction of immune responses to contact allergens, viral antigens and probably cutaneous tumor antigens (Teunissen, 1992). UVB radiation was shown to decrease the number of LC in the epidermis.

Ratis et al., 1998, have shown that exposure to UVB affects LC in at least two distinct pathways. Intercellular adhesion molecules-1 (ICAM-1) and especially CD 86 expression is significantly decreased. In addition, LC viability is reduced, which leads to apoptotic cell death. Both mechanisms contribute to UVB-induced immunosuppressive effects.

Besides LC, keratinocytes (KC) play an important role in UV-induced immunosuppression. UV-light affects production and secretion of immunomodulatory cytokines from KC, depending on its wavelength. Particularly IL-10 expression has been shown to play a major role in the induction of systemic immunosuppression and differential activation of T-helper subsets. Shreedar et al., 1998, described that prostaglandin $E_2$ ($PGE_2$) release of irradiated KC induces serum IL-4 which again induces IL-10 release. Thus, UV exposure activates a cytokine cascade resulting in systemic immunosuppression.

Recent results have demonstrated that UVA radiation also contributes to immunosuppression through an oxidative pathway (Iwai et al., 1999), suppressing the antigen-presenting function of epidermal cells, accompanied with suppression of the expression of costimulatory molecules on LC. It is postulated that this effect is mediated by reactive oxygen species.

Several hazardous effects are mediated by the immunosuppressive properties of UV radiation, as induction of apoptosis or programmed cell death. Apoptotic cells in the skin are called "sunburn cells" (Daniels et al., 1961; Young, 1987). Sunburn cells show some characteristic morphological changes: the dilated endoplasmatic reticulum forms vacuoles, chromatin is digested and condenses along the nuclear membrane often forming spheres, and dramatic cell shrinking is the most prevalent characteristic of apoptotic sunburn cells.

Numerous genes that encode mediators which regulate apoptosis have been identified, among them the tumor suppressor gene p53 and apoptosis inhibitor gene bcl-2 which are considered to play important roles. Wang et al., 1998, postulated that UVA and UVB initiate apoptosis by triggering two different signal transduction pathways. Whereas UVA, generating reactive oxygen species—mainly singlet oxygen—that cause lipid peroxidation (Kane et al., 1993) and disruption of membrane permeability, leads to immediate apoptosis through down-regulation of bcl-2 expression, UVB causes delayed apoptosis characterized by induction of DNA damage in the form of pyrimidine dimers and subsequent expression and accumulation of p53 proteins. There is increasing evidence that apoptosis may play an important role in immune reaction (Lynch et al., 1995).

Classical UV skin protectors which are used as sunscreens absorb UVA or UVB radiation directly on the skin surface. The protection provided is expressed by their Sun Protection Factor (SPF), which is the minimal dose at which an erythema is observed (Minimal Erythema Dose, MED) and which is highly dependent on the user's skin type. The use of such sunscreens is limited in that they only provide a certain degree of protection while being directly exposed to the sun. They have no regenerative effect, nor can they interact or prevent any UV-induced biochemical changes in the skin.

For a comprehensive photoprotection, especially against premature skin aging, photoallergies, immunosuppression and skin cancer, it is however necessary to reverse or reduce UV-induced biochemical changes in the skin. JP 05-017363 describes the anti-inflammatory effect produced by Lactobacillus, Bifidobacteria or their cell walls in relation to sunburn.

It is well established that UV exposure may cause dimerization of two adjacent pyrimidine molecules of the DNA. A cell-endogenous, enzymatically controlled excision repair system is able to repair such a damage as long as the damage frequency does not exceed the physiological repair capacity. If the repair capacity is insufficient, which could be the case in aging skin or after excessive UV exposure, cells with unrepaired DNA could be able to survive. The consequence can be chronic photodamage like dermal functional disorders with resultant premature aging, development of a precancerous stage of the cells or final development of skin carcinomas.

EP 0 043 128 B1 and U.S. Pat. No. 4,464,362 describe a cosmetic composition promoting the DNA repair process of the skin and which contains inactivated cultures of Bifidobacteria or bacteria related to this genus. Based on comprehensive in vitro and in vivo tests in animals as well as humans it has been established that the above composition, topically applied, significantly increases the DNA repair rate in UV-damaged cells. The above repair composition is a significant contribution to the art in that for the first time an agent is provided which can effectively prevent UV-induced DNA damage in skin cells.

As discussed above, however, UV-induced skin damage involves a cascade of pathophysiological events and is not limited to DNA damage. In the past few years it became apparent that UV-induced suppression of cell mediated immunity is another very important factor contributing to permanent skin damage including development of skin cancer and premature skin aging.

Fischer et al., 1998, describe molecular mechanisms of photoaging. UVR exposure results in the stimulation of cytokines released from keratinocytes or dermal fibroblasts. This leads to the activation of protein kinase signal transduction cascades, with the consequence of activation of transcription factor AP-1 which induces expression of matrix metalloproteinases (MMP). MMP's degrade the extracellular matrix in the dermis. ECM damage is followed by matrix repair, which is imperfect and thereby results in premature photoaging of the skin.

Thus, the problem underlying the present invention is to provide a cosmetic composition having significantly improved properties in that it minimizes or prevents chronic UV-induced photodamage in the skin on the DNA level by promoting the endogenous DNA repair mechanism as well as on the immunological level.

SUMMARY OF THE INVENTION

The invention relates to cosmetic compositions having an improved regenerative and protective effect on epidermal and dermal cells and their extracellular environment. Such compositions comprise a novel active complex of active ingredients, optimized to protect the skin from potentially harmful environmental effects.

The ingredients of the active complex according to the invention comprise inactivated bacteria selected from the group consisting of the genus of Bifidobacterium, Actinomycetaceae, Propionimycetaceae, Lactobacillaceae and Coryneform bacteria and a plant extracellular matrix composition, preferably prepared from soybean. The invention also provides a process for using such cosmetic compositions comprising the step of topically applying the cosmetic composition to the skin in order to prevent UV radiation induced damage.

DETAILED DESCRIPTION OF THE INVENTION

Figure 1:
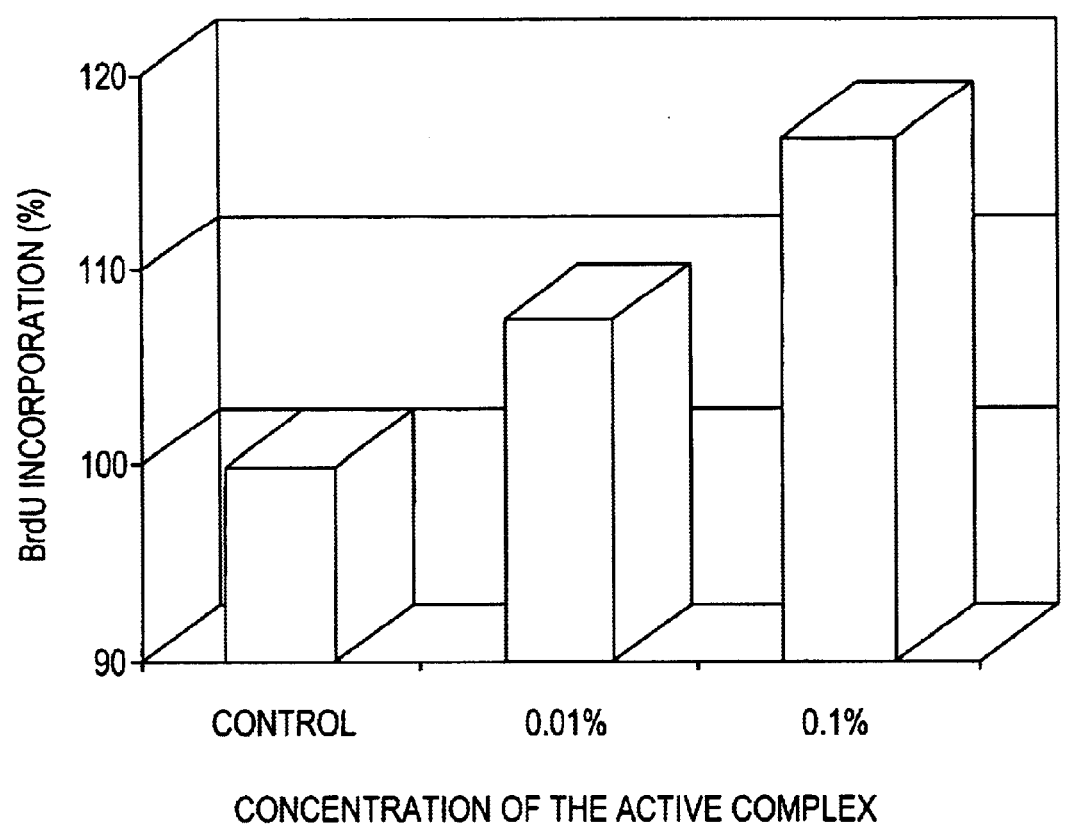
FIG. 1. Influence on DNA repair in keratinocytes. UV irradiation was applied to the keratinocytes.

While there have been reports that systemic or oral administration of either metabolites or fractions of Bifidobacteria may be used for immune modulation (DE 402 8 018, JP 01-242532 and JP 06-056618), there is no disclosure or evidence that the topical application of a composition such as described by above U.S. Pat. No. 4,464,362 will have any effect on UV-induced immunosuppression.

Unexpectedly, it has been found that a cosmetic composition comprising the biomass of Bifidobacteria or bacteria related to this genus which has been suspended and disintegrated in a plant extracellular matrix composition provides optimum protection against chronic UV-induced skin damage by acting against immunosuppression, preventing DNA strand breaks and restoring the equilibrium between skin cells and their extracellular environment.

EP 0 668 072 B1 and U.S. Pat. No. 5,547,997 which are hereby incorporated by reference disclose the composition and cosmetic use of a plant extracellular matrix. The primary cell wall of higher plants can be defined as a plant extracellular matrix. According to Roberts, 1990, the primary plant cell wall can consist of a number of protein fractions like the hydroxyproline-rich glycoproteins, repetitive proline-rich proteins, arabinoglactan proteins, extensins, solanaceous lectins, glycine-rich proteins, and thionins. In addition to protein fractions, the following components are usually present in the primary cell wall: pectin, xyloglycan, arabinoxylan, β1-3 and β1-4 glucans, cellulose, callose and lignin (see Roberts, 1989).

The plant cell wall consists of a structurally intricate network of polysaccharides and proteins. Recent research has shown how cell wall macromolecules, and fragments thereof, appear to be involved in processes such as cell growth, cell and tissue differentiation and the control of pathogenesis (Levy et al., 1992).

In search for similarities between the extracellular matrix of plant and animal cells it has been demonstrated, using cDNA probe and anti-human vitronectin antibodies, that lily, broadbean, soybean and tomato plants contain a 55 kD polypeptide that is related to vitronectin. This suggests that the vitronectin-like molecules may fulfill a role in cell adhesion and migration in a manner analogous to animal cells (Sanders et al., 1991).

High soy consumption leading to high exposures of soy isoflavones has been associated with a reduced risk of cancer. Isoflavones possess a variety of characteristics such as antioxidant, antiproliferative and differentiation-inducing abilities. The role of immune function has become increasingly important in the prevention of cancer (Zhang et al., 1997).

While cosmetic formulations containing the plant extracellular matrix were shown to counteract UV-induced premature skin aging by counteracting collagen crosslinking and to improve skin firmness and elasticity in humans, there is no disclosure or suggestion that such a plant matrix composition, topically applied, has any protective effect against UV-induced immunosuppression.

As outlined above, it has surprisingly been found that Bifidobacteria, disintegrated in a composition of a plant extracellular matrix, provide optimum protection against UV-induced skin alterations. Thus, in addition to preventing DNA strand breaks, the composition will also counteract UV-induced immunosuppression and maintain the integrity of the extracellular matrix.

This finding is unexpected and could not have been predicted based on the known properties of each of the individual components. The combined preparation of the active substance complex according to the invention provides an excellent cosmetic composition counteracting UV-induced DNA damage and immunosuppression. In view of this unique activity profile a new comprehensive approach to the prevention of UV-induced premature aging of the skin is provided.

The first component of the inventive active complex comprises inactivated bacteria of the genus Bifidobacteria, such as the species *Bifidobacterium longum* (Reuter) or other nonsporing gram-positive bacteria related to the genus Bifidobacterium as is described in EP 0 043 128 B1 and U.S. Pat. No. 4,464,362 which are hereby incorporated by reference. In one embodiment, the inactivated bacteria is selected from the group consisting of the genus Bifidobacterium, Actinomycetaceae, Propionimycetaceae, Lactobacillaceae and Coryneform bacteria. The first component contains the metabolic products, the cytoplasma fraction and cell wall constituents, like murein and polysaccharides.

The inactivated bacteria is obtained by the following process. Bacteria, such as Bifidobacteria are cultivated anaerobically in an appropriate medium, for example, under the conditions described in EP 0 043 128 B1 and U.S. Pat. No. 4,464,362. After reaching the early stationary phase, the bacteria culture is inactivated by pasteurization (at 60–65° C. for about 30 min). The bacteria are harvested by common separation techniques, for example, membrane filtration or centrifugation, resuspended in sterile physiological NaCl solution and separated again. The bacteria are washed with physiological NaCl solution two to three times and the biomass is collected and stored deep frozen.

Other suitable starting materials which can be used are bacteria related to the genus Bifidobacterium, such as listed e.g., in Bergery's Manual of Determinative Bacteriology, 8$^{th}$ Edition (1975) under Actinomycetaceae, Propionibacteriaceae, Lactobacillaceae and Coryneform bacteria (refer to, among others, pages 576, 599, 633 and 659 to 600).

The second component of the active substance complex according to the invention is a plant extracellular matrix composition from a plant selected from the group consisting of kelp, kudzu, maize, carrot, tomato, tobacco, bean, soybean, sugar beet, potato, melon and petunia. A particularly preferred source is soybean. Preferred extraction procedures are disclosed in EP-0-668072 on p. 4 line 42-p. 5 line 27.

Particularly preferred process steps for obtaining the second component are described below:

(a) The plant tissue, preferably from soybean, is minced and washed with an aqueous solution. The wash solution may further contain a preservative, for example, Phenonip preferably in a concentration of 0.3 to 0.4%;

(b) The minced and washed plant tissue is extracted under non-hydrolysing conditions with a solution preferably of 0.2 M $CaCl_2$, pH approximately 4, preserved with preferably 0.3 to 0.4% Phenonip. The ratio of plant tissue to extraction solution is preferably 1:10 (w/v). Extraction is continued for at least 24 hours under agitation at reduced temperature of about 5° C.; and (c) The insoluble material is removed from the extract by using conventional separation techniques, for example, centrifugation and final filtration preferably by using a 0.45 µm membrane.

The aqueous solution in step (a) may optionally comprise an antioxidant, such as metabisulfite ($Na_2S_2O_5$), preferably in a concentration of 4 mM. Any other concentration in the mM range is suitable. The optional antioxidant is washed out with an aqueous wash solution containing a preservative prior to step (b), for example, Phenonip preferably in a concentration of 0.3 to 0.4%.

The plant extracellular matrix composition obtained according to the invention obtainable by the above extraction procedures comprises one or more of the following in substantially native conformation: glycoproteins, including hydroxyproline-rich proteins (extensins); repetitive proline-rich proteins, arabinogalactan proteins, and lectins; and carbohydrate polymers selected from the group consisting of pectins, xyloglycans, arabinoglycans, glucans, calloses, lignins and combinations thereof.

The relative proportion of these plant extracellular matrix components in the extract depends upon the source of the extract, i.e., the type of plant used and on the extraction technique employed. For example, an extract of Kudzu leaves contains more hydroxyproline-rich glycoproteins than an extract from maize. However, in each case the components of extracellular matrix have substantially native conformation and are capable of mediating the biological function of the extracellular matrix, and thus are useful for cosmetic compositions.

The so prepared plant extracellular matrix composition in a preserved aqueous buffer can be directly used to resuspend the inactivated biomass of Bifidobacteria or bacteria related to this genus. The concentration of inactivated bacteria such as Bifidobacteria in the plant extracellular matrix extract is preferably in the range of 0.1 g/l to 10 g/l, more preferably about 0.4 g/l. This suspension can be disintegrated by ultrasound, mechanical procedures like cell milling, high-pressure homogenizing or by a combination of the mentioned procedures.

The active complex according to the invention (i.e., the inactivated Bifidobacteria homogenized as an endogenous part of the plant extracellular matrix composition) can be formulated in emulsified, aqueous and aqueous-alcoholic cosmetic preparations designed for topical application to the skin by means and methods well known to a person of ordinary skill in the art. The preferred dosage in a cosmetic composition is 0.1% to 10%, but is not limited to this range. In special cases the inventive active complex can be applied without a cosmetic carrier.

By the topical application of the cosmetic compositions according to the invention, UV radiation induced damage can be counteracted. The UV radiation induced damage is selected from the group consisting of permanent cell damage due to DNA damage and immunosuppression, premature skin aging process, reduction of cell viability, transformation to precancerous stage and formation of sunburn cells. The immunosuppression may be caused by enhanced IL-10 expression. The premature skin aging may be caused by enhanced MMP-1 expression.

The following formulations are exemplary embodiments of the invention, but are not intended to limit the scope of this invention or restrict it to these particular formulations.

EXAMPLE 1

Formation of Body Lotion

A body lotion (oil-in-water) containing the active composition comprises the following as listed in Table 1:

TABLE 1

| a) | PEG-7 hydrogenated castor oil | 2.00% |
|---|---|---|
| | PEG-20 glyceryl laurate | 1.00% |
| | cocoglycerides | 3.00% |
| | cetearyl alcohol | 1.00% |
| | cetearyl isononanoate | 4.00% |
| | octyl stearate | 4.00% |
| | phenoxyethanol (and) methylparaben (and) ethylparaben (and) butylparaben (and) propylparaben (and) isobutylparaben | 0.30% |
| b) | water, distilled | 73.40% |
| | phenoxyethanol (and) methylparaben (and) ethylparaben (and) butylparaben (and) propylparaben (and) isobutylparaben | 0.30% |
| | glycerin | 3.00% |
| c) | Bifidobacteria/plant extracellular matrix complex according to the present invention | 5.00% |
| d) | acrylamides copolymer (and) mineral oil (and) C13–C14 isoparaffin (and) polysorbate 85 | 3.00% |

Mixture a) is melted at approximately 70° C. and mixture b) is heated to approximately 70° C. and added to mixture a) while stirring. Stirring is continued until the lotion has cooled down to approximately 30° C. Then composition c) and d) are added while stirring, the lotion is homogenized.

EXAMPLE 2

Formation of Gel-Lotion

A gel-lotion containing the active composition comprises the following as listed in Table 2:

TABLE 2

| a) | acrylamides copolymer (and) mineral oil (and) C13–14 isoparaffin (and) polysorbate 85 | 5.00% |
|---|---|---|
|  | myreth-3 myristate | 4.00% |
| b) | water, distilled | 85.00% |
|  | phenoxyethanol (and) methylparaben (and) ethylparaben (and) butylparaben (and) propylparaben (and) isobutylparaben | 0.50% |
|  | xanthan gum | 0.50% |
| c) | Bifidobacteria/plant extracellular matrix complex according to the present invention | 5.00% |

Mixture a) is dissolved at approximately 50° C. Mixture b) is dispersed at room temperature and added to a) while stirring. Then, composition c) is added thereto while stirring.

EXAMPLE 3

Formation of Oil-in-water Cream

A cream (oil-in-water) containing the active composition comprises the following as listed in Table 3.

TABLE 3

| a) | cetearyl alcohol (and) ceteareth-20 | 8.00% |
|---|---|---|
|  | cocoglycerides | 2.00% |
|  | cetearyl alcohol | 2.00% |
|  | dicaprylyl ether | 8.00% |
|  | oleyl erucate | 7.00% |
|  | phenoxyethanol (and) methylparaben (and) ethylparaben (and) butylparaben (and) propylparaben (and) isobutylparaben | 0.30% |
| b) | water, distilled | 62.40% |
|  | phenoxyethanol (and) methylparaben (and) ethylparaben (and) butylparaben (and) propylparaben (and) isobutylparaben | 0.30% |
|  | glycerin | 5.00% |
| c) | Bifidobacteria/plant extracellular matrix complex according to the present invention | 5.00% |

Mixture a) is melted at approximately 70° C. and mixture b) is likewise heated to approximately 70° C. and added to mixture a) while stirring. Stirring is continued until the cream has cooled down to approximately 30° C. Then, composition c) is added while stirring and the cream is homogenized.

EXAMPLE 4

Formation of Water-in-oil Cream

A cream (water-in-oil) containing the active composition comprises the following as listed in Table 4:

TABLE 4

| a) | diisostearoyl polyglyceryl-3 dimer dilinoleate | 3.00% |
|---|---|---|
|  | beeswax | 0.60% |
|  | castor oil, hydrated | 0.40% |
|  | paraffinum subliquidum | 5.00% |
|  | isohexadecane | 10.00% |
|  | PPG-15 stearyl ether | 2.00% |

TABLE 4-continued

|  | dimethicone | 0.50% |
|---|---|---|
|  | phenoxyethanol (and) methylparaben (and) ethylparaben (and) butylparaben (and) propylparaben (and) isobutyparaben | 0.30% |
| b) | water, distilled | 68.40% |
|  | phenoxyethanol (and) methylparaben (and) ethylparaben (and) butylparaben (and) propylparaben (and) isobutylparaben | 0.30% |
|  | glycerin | 3.00% |
|  | $MgSO_4 \times 7H_2O$ | 1.00% |
| c) | Bifidobacteria/plant extracellular matrix complex according to the present invention | 5.00% |
| d) | silica dimethyl silylate | 0.50% |

Mixture a) is heated to approximately 80° C., mixture b) is likewise brought to 80° C. and added to a) while stirring. Stirring is continued until the cream has cooled down to approximately 30° C. c) and d) are added. The cream is homogenized by a roller.

The combined active complex showed unexpectedly high effectiveness, in relation to what could be expected from the known effects of the single components.

The below described experiments clearly demonstrate the beneficial effect of the Bifidobacteria/plant extracellular matrix complex according to the invention against UV radiation induced skin damage.

EXAMPLE 5

Influence on DNA Repair in Keratinocytes

For the investigation of the influence of active complex of the invention on DNA repair the Cell Proliferation ELISA, BrdU (obtainable from Roche; 1647229) was used.

Brief Description of the Assay Procedure

Human keratinocytes (HaCaT), grown in DMEM+5% FCS+L-Glutamin+Gentamycin (culture medium), in stationary growth phase were trypsinized and a cell suspension of $3\times10^5$ cells/ml was prepared.

The obtained cell suspension was seeded on microtiter plates using 50 µl/well ($1.5\times10^4$ cells/well). Sample dilutions (0.01%, 0.1%) of the active complex according to the invention were prepared using the FCS-free culture medium and 50 µl of either of these dilutions were filled into the proper wells; as control FCS-free culture medium was used only. The plate was incubated in the $CO_2$ incubator at 37° C. for 72 hrs. Then the supernatant was removed and each well was washed twice with 200 µl of PBS per well. 50 µl of PBS were added to the cells in each well which were then irradiated (2 $J/cm^2$ UVA+0.2/$cm^2$ UVB). The supernatant was removed and substituted with FCS-free culture medium (100 µl/well). After adding the BrdU solution (10 µl/well) the plates were incubated in the $CO_2$ incubator at 37° C. for 18 hrs. Then the medium was removed and the cells washed and fixed. Then the anti-BrdU-POD antibody was incubated at ambient temperature for 2 hrs (100 µl/well of antibody solution). The plates were washed and the substrate solution (100 µl/well) was added (approx. 20 min). The assay was terminated by the addition of 50 µl/well 1 M $H_2SO_4$ and the OD values were read at 450 nm (reference: 630 nm).

As shown in FIG. 1 the inventive product increases incorporation of bromodeoxyuridine (BrdU) in the DNA by up to 18% after UV irradiation of keratinocytes, whereby the BrdU level is a direct measure of DNA repair.

EXAMPLE 6

Influence on Formation of DNA Fragments (Nucleosomes) after UV Irradiation

For the determination of the formation of DNA fragments the Cell Death Detection ELISA (obtainable from Roche, 1774425) was employed.

Brief Description of the Assay Procedure

Human keratinocytes (HaCaT), grown in DMEM+5% FCS+L-Glutamin+Gentamycin (culture medium), in stationary growth phase were trypsinized and a cell suspension of $3 \times 10^5$ cells/ml was prepared. The obtained cell suspension was seeded on microtiter plates using 50 µl/well ($1.5 \times 10^4$ cells/well). Sample dilutions (0.05%, 0.1%) of the active complex according to the invention were prepared using the FCS-free culture medium and 50 µl of either of these dilutions were filled into the proper wells; as control FCS-free culture medium was used only. The plate was incubated in the $CO_2$ incubator at 37° C. for 72 hrs. Then the supernatant was removed and each well was washed twice with 200 µl of PBS per well. 50 µl PBS were added to each well and the plate irradiated (1 $J/cm^2$ UVA+0.1/$cm^2$ UVB). The supernatant was removed and substituted by FCS-free culture medium (100 µl/well). Then the plate was incubated in the $CO_2$ incubator at 37° C. for 18 hrs. Afterwards the cells were lysed with 200 µl lysis reagent and centrifuged at 200×g for 10 min. The resulting supernatant was filled in a microtiter plate and the nucleosomes were detected using an anti-histone-biotin antibody and an anti-DNA-POD antibody (Cell Death Detection ELISA (Roche; 1774425). The OD values were read at 405 nm (reference: 490 nm)

Figure 2:
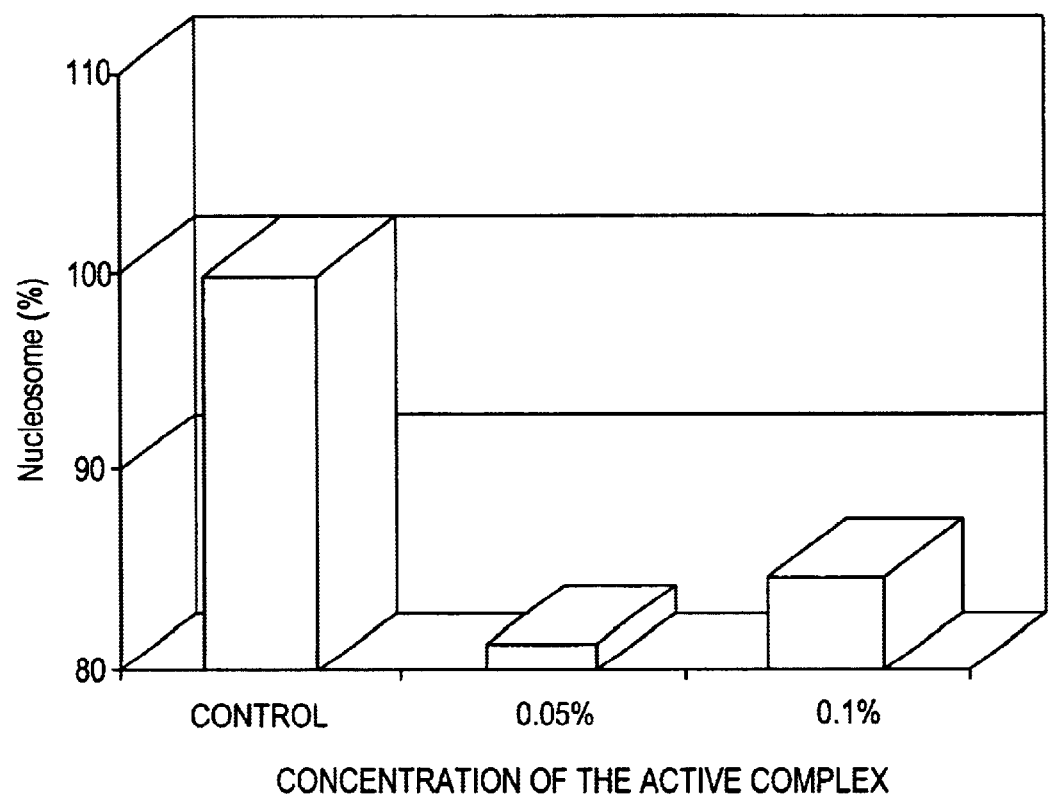
FIG. 2. Influence on formation of DNA fragments (nucleosomes) after UV irradiation.

As demonstrated in FIG. 2 the active complex according to the invention prevents formation of DNA double strand breaks (nucleosomes) after UV irradiation.

EXAMPLE 7

Influence on Cell Viability of Keratinocytes after UV Irradiation (MTT Assay)

Brief Description of the Assay Procedure

Human keratinocytes (HaCaT), grown in DMEM+5% FCS+L-Glutamin+Gentamycin (culture medium), in stationary growth phase were trypsinized and a cell suspension of $3 \times 10^5$ cells/ml was prepared. The obtained cell suspension was seeded on microtiter plates using 50 µl/well ($1.5 \times 10^4$ cells/well). Sample dilutions (0.01%, 0.05%, 0.1%, 0.5%) of the active complex according to the invention were prepared using the FCS-free culture medium and 50 µl of either of these dilutions were filled into the proper wells; as control FCS-free culture medium was used only. The plate was incubated in the $CO_2$ incubator at 37° C. for 72 hrs. Then the supernatant was removed and each well was washed twice with 200 µl PBS per well. 50 µl PBS were added to each well and the plate was irradiated (2 $J/cm^2$ UVA+0.2/$cm^2$ UVB). Then the supernatant was removed and 100 ml/well FCS-free medium was added. The plate was then incubated in the $CO_2$ incubator at 37° C. for 18 hrs. 10 µl MTT solution (5 mg of PBS per ml) were added to each well and the plate was incubated at 37° C. for 4 hrs (10% $CO_2$). The supernatant was removed and 100 µl acidic SDS/DMSO solution was added to each well. The OD values were read at 570 nm. The absorbance values of non-irradiated cells were used as a reference.

Figure 3:
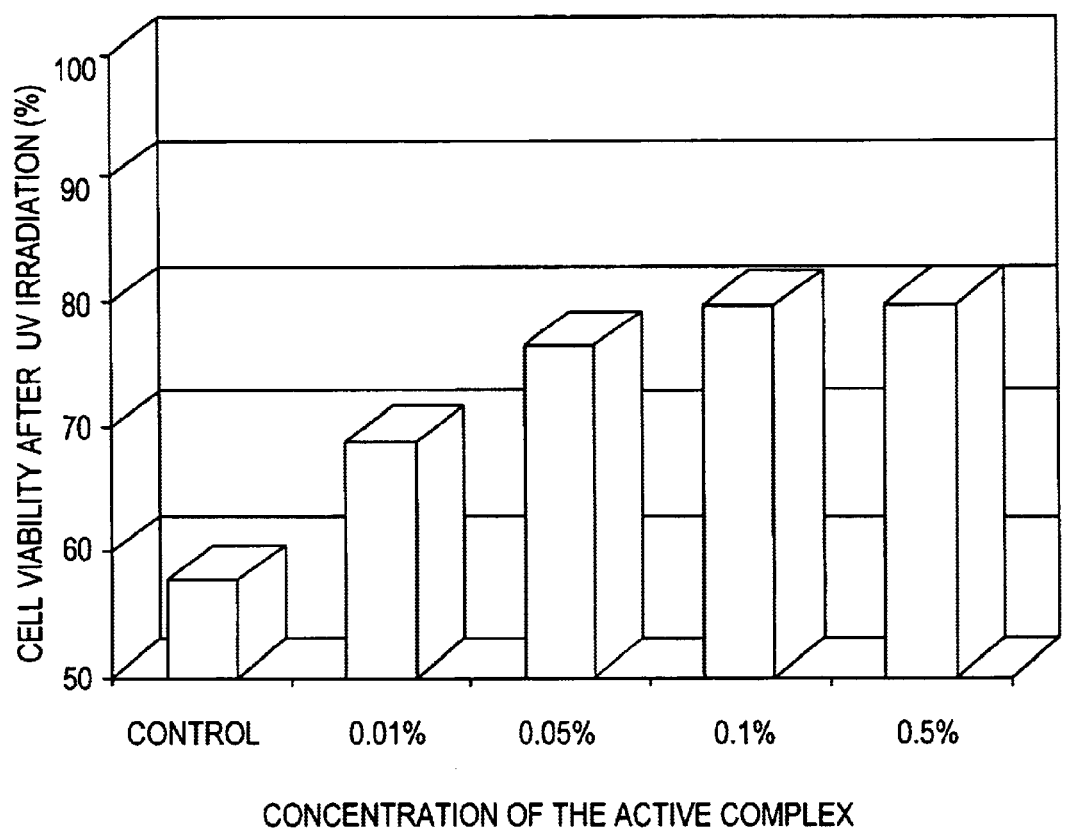
FIG. 3. Influence on cell viability of keratinocytes after UV irradiation (MTT assay).

As shown in FIG. 3 the active complex according to the invention counteracts the reduction of cell viability after UV irradiation.

EXAMPLE 8

Influence on Interleukin-10 Expression after UV Irradiation of Keratinocytes Brief Description of the Assay Procedure Human keratinocytes (HaCaT), grown in DMEM+5% FCS+L-Glutamin+Gentamycin (culture medium), in stationary growth phase were trypsinized and a cell suspension of $3 \times 10^5$ cells/ml was prepared. The obtained cell suspension was seeded on microtiter plates using 50 µl/well ($1.5 \times 10^4$ cells/well). Sample dilutions (0.01%, 0.1%) of the active complex according to the invention were prepared using the FCS-free culture medium and 50 µl of either of these dilutions were filled into the proper wells; as control FCS-free culture medium was used only. The plate was incubated in the $CO_2$ incubator at 37° C. for 72 hrs. Then the supernatant was removed and each well was washed twice with 200 µl PBS per well. Then 50 µl PBS was added to each well and and the plate was irradiated (2 $J/cm^2$ UVA+0.2/$cm^2$ UVB). The supernatant was removed and 100 ml/well FCS-free medium was added. The plate was incubated in the $CO_2$ incubator at 37° C. for 12 hrs, then the medium was removed and the cells washed and fixed. The anti-IL-10 antibody was incubated at 37° C. for 2 hrs, then the plate was washed. The anti-mouse-IgG-biotin antibody was incubated at 37° C. for 1 hr, then the plate was washed again. The plate was incubated with the streptavidin-POD complex at 37° C. for 1 hr, after further washing the substrate solution (ABTS) was added. The reaction was stopped with 50 µl/well 1 M $H_2SO_4$ and the OD values were read at 450 nm (reference: 630 nm).

Figure 4:
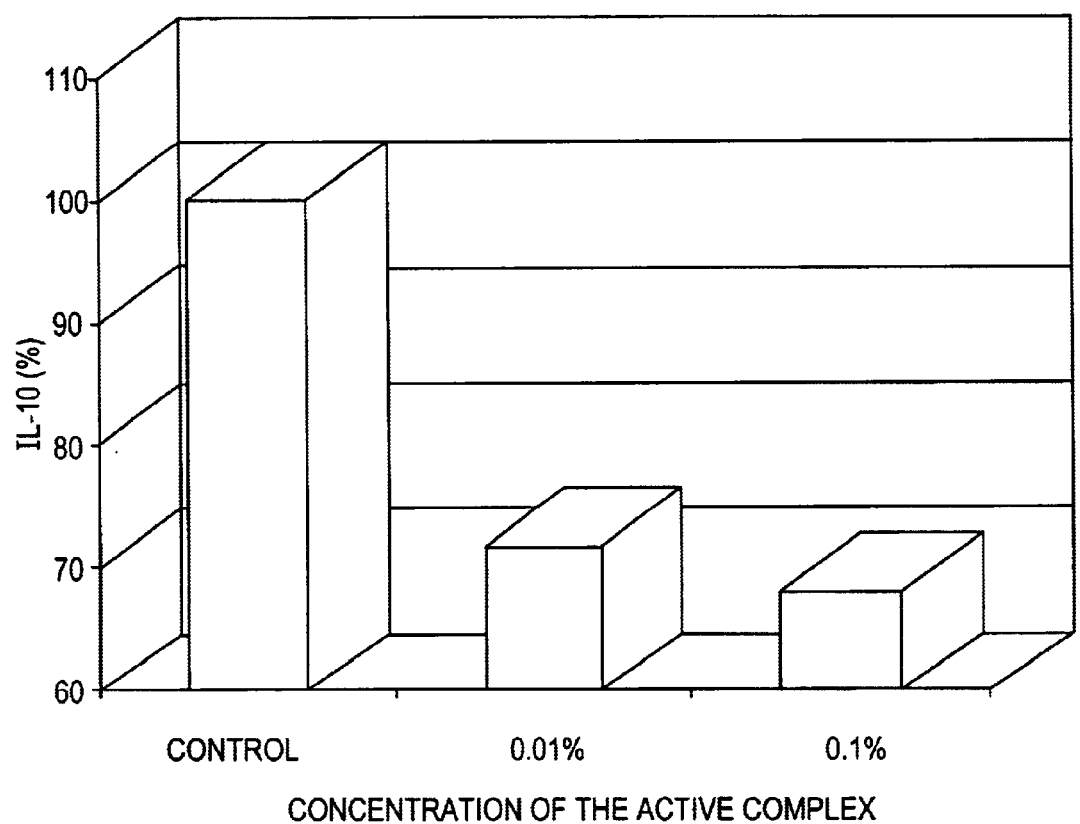
FIG. 4. Influence on interleukin-10 expression after UV irradiation of keratinocytes.

FIG. 4 demonstrates that the active complex according to the invention reduces IL-10 expression by UV irradiated keratinocytes by about 30%, thus counteracting systemic immunosuppression.

EXAMPLE 9

Effect on Interleukin-10 Secretion by Human Monocytes

The influence on IL-10 secretion was determined by the Quantikine™ human IL-10 ELISA (obtainable from R&D Systems, Wiesbaden, Germany).

Brief Description of the Assay Procedure

Monocytes and lymphocytes from peripheral blood obtained from a healthy volunteer were isolated by density gradient isolation (Polymorphprep™). The monocytes were separated by incubation of monocytes and lymphocytes in RPMI 1640 medium with 10% FCS for 2 hrs, whereby the monocytes adhered to the culture plates. The active complex according to the invention (0.01% and 0.001%) was added to monocytes ($1.75 \times 10^5$ cells/200 µl/well) stimulated by 10 µg of lipopolysaccharides (LPS). Monocytes stimulated by 10 µg/ml LPS served as a positive control. The monocytes were cultured for 18 hrs (37° C., 10% $CO_2$). The IL-10 in cell culture supernatants was quantified by a commercially available sandwich ELISA (Quantikine™ human IL-10 ELISA obtained from R&D Systems, Wiesbaden, Germany), which was carried out in duplicate.

Figure 5:
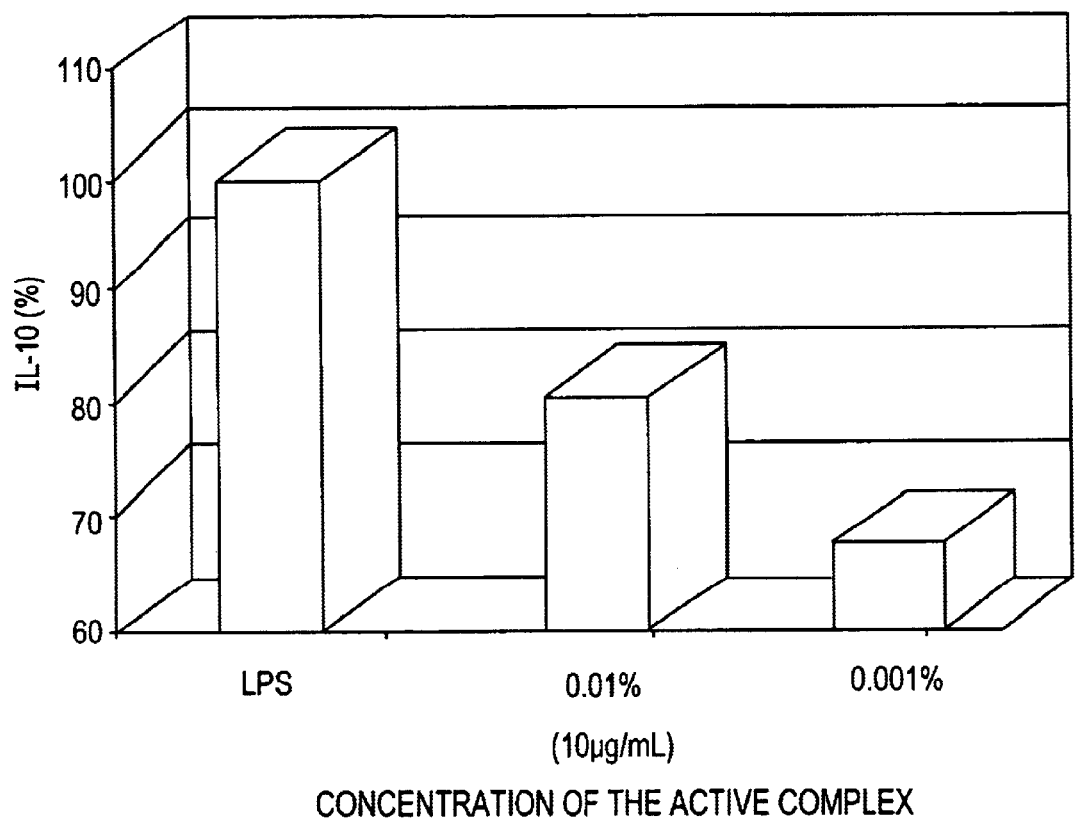
FIG. 5. Effect on interleukin-10 secretion by human monocytes.

UV-exposure results in systemic immunosuppression mediated by IL-10 secreted by monocytes. In this connection, it could be shown that the active complex according to the invention decreases IL-10 secretion of stimulated monocytes in a dose dependent manner as demonstrated in FIG. 5.

EXAMPLE 10

Influence on Matrix Metalloproteinase-1 (MMP-1) after UV Irradiation

The expression of MMP-1 after UV irridiation was determined using the MMP-1 Activity Assay System (obtained from Biotrak [Amersham Pharmacia]; RPN 2629).

Brief Description of the Assay Procedure

Human keratinocytes (HaCaT), grown in DMEM+5% FCS+L-Glutamin+Gentamycin (culture medium), in stationary growth phase were trypsinized and a cell suspension of $3\times10^5$ cells/ml was prepared. The obtained cell suspension was seeded on microtiter plates using 50 µl/well (1.5× $10^4$ cells/well). Sample dilutions (0.1%, 0.5%) of the active complex according to the invention were prepared using the FCS-free culture medium and 50 µl of either of these dilutions were filled into the proper wells; as control FCS-free culture medium was used only. The plate was incubated in the $CO_2$ incubator at 37° C. for 72 hrs. Then, the supernatant was removed and each well was washed twice with 200 µl of PBS per well. 50 µl PBS was added to each well, then the plate was irradiated (1 J/cm² UVA+0.1/cm² UVB). The supernatant was removed and FCS-free culture medium (100 µl/well) was added, then the plate was incubated in the $CO_2$ incubator at 37° C. for 48 hrs. Then, 100 µl of the supernatant was added to the proper wells of the test plate coated with anti-MMP-1 which was then incubated at 4° C. for 18 hrs. The plate was washed and detection solution (50 µl/well) as well as 50 µl of test buffer (add APMA solution instead of test buffer to standard) were added. After short shaking, the plate was read at 405 nm ($Abs_{t=0}$). After incubation at 37° C. for 6 hrs the plate was read again at 405 nm ($Abs_{t=6}$). The expression of active MMP-1 was calculated using the formula below:

$$\frac{(Abs_{t=6} - Abs_{t=0}) \times 1000}{h^2}$$

Figure 6:
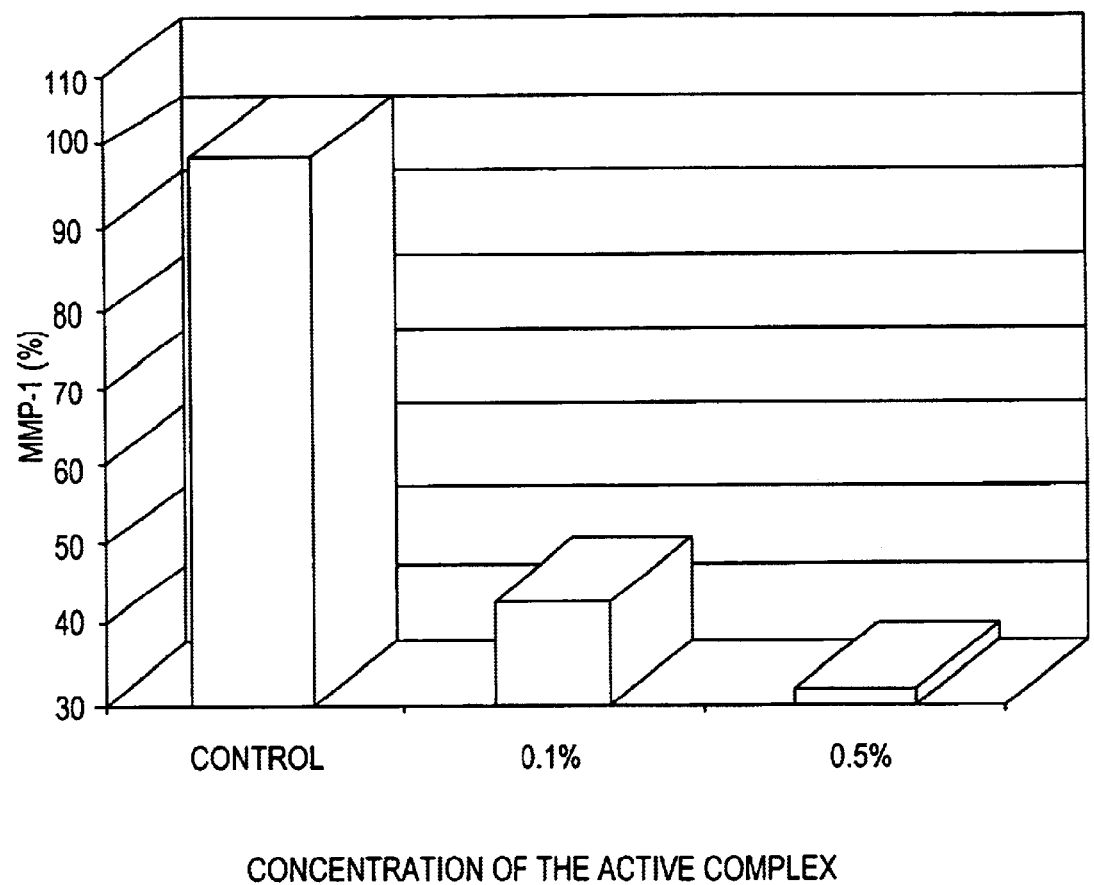
FIG. 6. Influence on matrix metalloproteinase-1 after UV irradiation.

As shown in FIG. 6 the active complex according to the invention reduces expression of MMP-1 after UV irradiation of human keratinocytes by up to 68% compared to the control. The reduction of MMP-1 activity represents protection against hydrolytic cleavage of triple-helical collagen of the types I, II and III.

The results of above tests clearly indicate that the Bifidobacteria/plant extracellular matrix complex according to the invention is particularly efficient for counteracting UV-induced damage of skin cells.

Although the present invention has been described in detail with reference to examples above, it is understood that various modifications can be made without departing from the spirit of the invention. Therefore, it will be appreciated that the scope of this invention is to be defined by the appended hereto, rather than the specific embodiments which have been presented hereinbefore by way of example.

Literature

Baadsgard, O.: In vivo ultraviolet irradiation of human skin results in profound perturbation of the immune system. *Arch Dermatol* 127:99–109, 1991.

Daniels, F., Jr., D. Brophy and W. C. Lobitz Jr.: Histochemical responses of human skin following ultraviolet irradiation. *J Invest Dermatol* 37:351–356, 1961.

Denkins, Y. D., I. J. Fidler and M. L. Kripke: Exposure of mice to UV-B radiation suppresses delayed hypersensitivity to *Candida albicans*. *Photochem Photobiol* 49:615–619, 1989.

Fisher, G. J. and J. J. Voorhees: Molecular Mechanisms of Photoaging and its Prevention by Retinoic Acid: UVR Induces MAP Kinase Signal Transduction Cascades that Induce AP-1 Regulated Matrix Metalloproteinases that Degrade Human Skin In Vivo. *J Invest Dermatol, Symposium Proceedings* 3: 61–68, 1998.

Giannini, M. S.: Suppression of pathogenesis in cutaneous leishmaniasis by UV-irradiation. *Infect Immunol* 51:838–843, 1986.

Iwai, I., M. Hatao, M. Naganuma, Y. Kumano and M. Ichihashi: UVA-induced immune suppression through an oxidative pathway. *J Invest Dermatol* 112 (1):19–24, 1999.

Jeevan, A. and M. L. Kripke: Effect of a single exposure to UVB radiation on Mycobacterium bovis bacillus Calmette-Guerin infection in mice. *J Immunol* 143:2837–2843, 1989.

Kane, D. J., T. A. Sarafin, S. Auton et al.: Bcl-2 inhibition of neural cell death: decreased generation of reactive oxygen species. *Science* 262:1274–1276, 1993.

Kripke, M. L.: Immunological unresponsiveness induced by UV radiation. *Immunol Rev* 80:87–102, 1984.

Kvam, E. and R. M. Tyrrell: Induction of oxidative DNA base damage in human skin cells by UV and near visible radiation. *Carcinogenesis* 18:2379–2384, 1997.

Levy, S., L. A. Staehelin: Synthesis, assembly and function of plant cell wall macromolecules. *Current Opinion in Cell Biology* 4:856–862, 1992.

Lynch, D. H., F. Ramsdell and M. R. Alderson: Fas and FasL in the homeostatic regulation of immune responses. *Immunol Today* 16:569–574, 1995.

Miller et al. *Biochem* 11:4903, 1972.

Otani, T. and R. Mori: The effects of ultraviolet irradiation of the skin on herpes simplex virus infection: alteration in immune function mediated by epidermal cells and in the course of infection. *Arch Virol* 96:1–15, 1987.

Rattis et al.: Effects of UVB Radiation on Human Langerhans Cells: Functional Alteration of CD 86 Upregulation and Induction of Apoptotic Cell Death. *J Invest Dermatol* 111:373–379, 1998.

Roberts, K. *Curr Op Cell Biol* 1:1020–1027, 1989.

Roberts, K. *Curr Op Cell Biol* 2:920–928, 1990.

Sanders, L. C., C. S. Wang, L. L. Walling, E. M. Lord: Homologes of the Substrate Adhesion Molecule Vitronectin occurs in four Species of Flowering Plants. *Plant Cell* 3:629–635, 1991.

Shreedar, V., T. Giese, V. W. Sung and S. E. Ullrich: A cytokine cascade including prostaglandin E2, IL-4, and IL-10 is responsible for UV-induced systemic immune suppression. *J Immunol* 160 (8):3783–3789, 1998.

Teunissen, M. B. M.: Dynamic nature and function of epidermal Langerhans cells in vivo and in vitro: a review, with emphasis on human Langerhans cells. *Histochem J* 24:697–716, 1992.

Wang, Y. et al.: Differential Regulation of P53 and Bcl-2 Expression by UV A and B. *J Invest Dermatol* 111:380–384, 1998.

Young, A. R.: The sunburn cell. *Photodermatol* 4:127–134, 1987.

Zhang, R., Y. Li, W. Wang: *Nutrition and Cancer* 29 (1): 24–28, 1997.

We claim:

1. A cosmetic composition comprising a cosmetically effective amount of a first component which comprises inactivated bacteria selected from the group consisting of the genus Bifidobacterium, Actinomycetaceae, Propionimycetaceae, Lactobacillaceae and Coryneform bacteria and a cosmetically effective amount of a second component which comprises an extract of plant extracellular matrix, wherein said inactivated bacteria is disintegrated in said extract of plant extracellular matrix.

2. The cosmetic composition according to claim 1, wherein the plant extracellular matrix is from a plant selected from the group consisting of kelp, kudzu, maize, carrot, tomato, tobacco, bean, soybean, sugar beet, potato, melon and petunia.

3. The cosmetic composition according to claim 1, wherein the plant extracellular matrix is from a soybean plant.

4. The cosmetic composition according to claim 1, wherein the plant extracellular matrix is derived from primary or secondary plant cell wall.

5. The cosmetic composition according to claim 1, wherein the extract of the plant extracellular matrix is selected from the group consisting of glycoproteins, hydroxyproline-rich proteins, repetitive proline-rich proteins, carbohydrate polymers, arabinogalactan proteins, lectins and mixtures thereof.

6. The cosmetic composition according to claim 5, wherein the carbohydrate polymers are selected from the group consisting of pectins, xyloglycans, arabinoglycans, glucans, calloses, lignins and mixtures thereof.

7. The cosmetic composition according to any one of claims 1 to 6, wherein the inactivated bacteria is obtained by a process comprising the steps of:

(a) culturing the bacteria under anaerobic conditions in an appropriate medium;

(b) inactivating the culture of bacteria by pasteurization after the culture reaches the early stationary phase; and (c) harvesting inactivated bacteria from the culture and washing the bacteria with a physiological NaCl solution.

8. The cosmetic composition according to any one of claims 1 to 6, wherein the extract of the plant extracellular matrix is obtained by a process comprising the steps of:

(a) mincing and washing the plant tissue with an aqueous solution;

(b) extracting the minced and washed plant tissue under non-hydrolysing conditions to produce a plant extract; and (c) removing the insoluble material from the extract to produce an extract of plant extracellular matrix.

9. The cosmetic composition according to claim 8, wherein the aqueous solution further comprises an antioxidant and a preservative, wherein the antioxidant is removed from the solution prior to step (b).

10. The cosmetic composition according to any one of claims 1 to 6, wherein the concentration of the inactivated bacteria in the extract of plant extracellular matrix is 0.1 g/l to 10 g/l.

11. The cosmetic composition according to any one of claims 1 to 6, wherein the concentration of the inactivated bacteria in the extract of plant extracellular matrix is 0.4 g/l.

12. The cosmetic composition according to claim 1, wherein the inactivated bacteria is disintegrated by ultrasound, by a mechanical technique, or by a combination thereof.

13. A process for using the cosmetic composition according to claim 1 comprising the step of topically applying the cosmetic composition to skin in order to prevent UV radiation induced damage to the skin.

14. The process according to claim 13, wherein the UV radiation induced damage is selected from the group consisting of immunosuppression, DNA-damage, reduction of cell viability, transformation to precancerous stage, formation of sunburn cells and premature skin aging.

15. The process according to claim 13, wherein the UV radiation induced damage is immunosuppression.

16. The process according to claim 14 or 15, wherein the immunosuppression is caused by enhanced IL-10 expression.

17. The process according to claim 14, wherein the premature skin aging is caused by enhanced MMP-1 expression.

18. The cosmetic composition according to claim 1, wherein the inactivated bacteria is of the genus Bifidobacterium.

19. The cosmetic composition according to claim 1, wherein the inactivated bacteria is *Bifidobacterium Longum*.

20. The cosmetic composition according to claim 1, wherein the inactivated bacteria is disintegrated in a cell mill or by high pressure homogenizing.

* * * * *